(12) United States Patent
Nennig et al.

(10) Patent No.: US 10,828,145 B2
(45) Date of Patent: Nov. 10, 2020

(54) STENT FOR USING IN BIFURCATIONS

(71) Applicant: Medfirst AG, Balzers (LI)

(72) Inventors: Ernst Nennig, Karlsruhe (DE); Harald Fischer, Weingarten (DE)

(73) Assignee: Medfirst AG, Balzers (LI)

( * ) Notice: Subject to any disclaimer, the term of this patent is extended or adjusted under 35 U.S.C. 154(b) by 20 days.

(21) Appl. No.: 16/083,459

(22) PCT Filed: Feb. 9, 2017

(86) PCT No.: PCT/EP2017/052847
§ 371 (c)(1),
(2) Date: Sep. 7, 2018

(87) PCT Pub. No.: WO2017/153116
PCT Pub. Date: Sep. 14, 2017

(65) Prior Publication Data
US 2019/0069985 A1  Mar. 7, 2019

(30) Foreign Application Priority Data
Mar. 9, 2016  (DE) .................. 10 2016 104 302

(51) Int. Cl.
*A61F 2/07* (2013.01)
*A61F 2/954* (2013.01)
(Continued)

(52) U.S. Cl.
CPC .................. *A61F 2/07* (2013.01); *A61F 2/88* (2013.01); *A61F 2/915* (2013.01); *A61F 2/954* (2013.01);
(Continued)

(58) Field of Classification Search
CPC ...... A61F 2/82; A61F 2/954; A61F 2002/065; A61F 2/07; A61F 2/06
See application file for complete search history.

(56) References Cited

U.S. PATENT DOCUMENTS

| 5,893,887 A | 4/1999 | Jayaraman |
| 6,264,686 B1 | 7/2001 | Rieu et al. |

(Continued)

FOREIGN PATENT DOCUMENTS

| DE | 696 28 595 T2 | 6/2004 |
| DE | 696 29 599 T2 | 6/2004 |

OTHER PUBLICATIONS

German search report dated Nov. 18, 2016 in corresponding German patent application No. 10 2016 104 302.8 (two pages).
(Continued)

*Primary Examiner* — Jason-Dennis N Stewart
(74) *Attorney, Agent, or Firm* — Kilpatrick Townsend & Stockton LLP

(57) ABSTRACT

Disclosed is a stent for transluminal implantation in hollow organs, particularly in blood vessels, the ureter, the esophagus, the colon, the duodenum or bile ducts. The stent comprises a first section comprising a substantially tubular first body which extends along a first longitudinal axis and comprises a first lateral end and a first central end; a second section comprising a substantially tubular second body which extends along a second longitudinal axis and comprises a second lateral end and a second central end, wherein the first and second stent sections are connected to each other in the region of the central ends by means of a coupling section, the stent comprising a plurality of cells which are defined by bordering elements formed by the tubular bodies, and wherein the first central end of the first stent section is embodied in a sloping manner.

21 Claims, 1 Drawing Sheet

Figure 1:
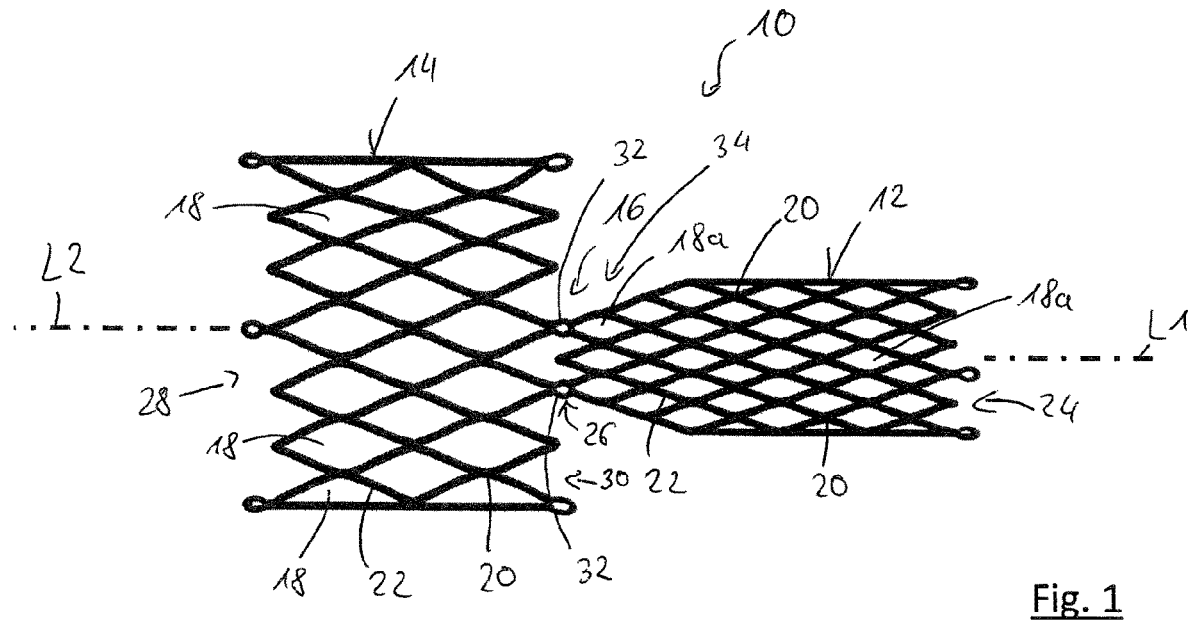

(51) Int. Cl.
*A61F 2/915* (2013.01)
*A61F 2/88* (2006.01)
*A61F 2/82* (2013.01)
*A61F 2/06* (2013.01)
*A61F 2/90* (2013.01)
*A61F 2/04* (2013.01)

(52) U.S. Cl.
CPC ........... *A61F 2/90* (2013.01); *A61F 2002/041* (2013.01); *A61F 2002/044* (2013.01); *A61F 2002/048* (2013.01); *A61F 2002/061* (2013.01); *A61F 2002/828* (2013.01)

(56) References Cited

U.S. PATENT DOCUMENTS

| | | |
|---|---|---|
| 2001/0039448 A1 | 11/2001 | Dibie |
| 2004/0176833 A1* | 9/2004 | Pavcnik ................ A61F 2/07 623/1.13 |
| 2006/0265050 A1 | 11/2006 | Morris et al. |
| 2008/0132989 A1 | 6/2008 | Snow et al. |
| 2010/0049307 A1 | 2/2010 | Ren |
| 2011/0004291 A1 | 1/2011 | Davis et al. |
| 2011/0218617 A1 | 9/2011 | Nguyen et al. |
| 2012/0116500 A1 | 5/2012 | Jang et al. |
| 2015/0081007 A1 | 3/2015 | Joye et al. |

OTHER PUBLICATIONS

International Search Report dated Apr. 21, 2017 in corresponding PCT Application No. PCT/EP2017/052847 (four pages).

* cited by examiner

STENT FOR USING IN BIFURCATIONS

This application is a U.S. National Phase Application of PCT/EP2017/052847, filed Feb. 9, 2017, which claims the priority of German Patent Application 10 2016 104 302.8, filed Mar. 9, 2016, the entireties of which are incorporated by reference herein.

The present invention relates to a stent for transluminal implantation into hollow organs, in particular into blood vessels, ureters, esophagi, the colon, the duodenum, or bile ducts, comprising a first stent section having a substantially tubular first body that extends along a first longitudinal axis and that has a first lateral end and a first central end. The stent furthermore comprises a second stent section having a substantially tubular second body that extends along a second longitudinal axis and that has a second lateral end and a second central end. The first stent section and the second stent section are here connected to one another by means of a coupling section in the region of the central ends and the stent comprises a plurality of cells that are defined by bordering elements formed by the tubular bodies, wherein the tubular bodies can each be transformed from a compressed state having a first cross-section diameter into an expanded state having an increased second cross-section diameter.

Stents of this type are used for the recanalization of pathologically altered hollow organs, wherein the use in particular takes place at branches, i.e. at bifurcations. The first stent section can, for example, be deployed in a branch of a hollow organ having a smaller diameter, whereas the second stent section can be arranged in a lumen of the hollow organ having a larger diameter.

To deploy the stent, the stent sections are introduced in the compressed state via a common delivery catheter to the position within the hollow organ to be treated where they are expanded by different measures to a diameter which corresponds to the diameter of the healthy hollow organ so that a supporting effect of the hollow organ, for example of a vessel wall, is achieved.

Such stents can e.g. be produced in that openings such as slits are cut into the wall of a tubular body and extend partly in the longitudinal axis of the stent so that diamond-shaped openings, for example, are produced on the expansion of the stent. An opening together with its bordering elements is called a cell.

On the use of stents having two stent sections at bifurcations of a hollow organ, one stent section can project into the lumen of the hollow organ, which is not wanted since deposits can easily accumulate at the projecting part of the stent and can result in the clogging of e.g. blood vessels.

It is therefore the underlying object of the invention to provide a stent of the initially named kind that suppresses a clogging at bifurcations, with the stent simultaneously providing a high radial placement force to reliably prevent the kinking of the stent on its deployment.

This object is satisfied in accordance with the invention by a stent having the features of claim 1 and in particular in that the first central end of the first stent section is chamfered.

It is made possible by the chamfered first central end that the first central end adapts to the shape of the bifurcation of the hollow organ, in particular when the bifurcation is arranged at a slant to a main lumen of the hollow organ. That part of the first stent section is therefore reduced by the chamfer that would conventionally project into the lumen of the hollow organ on deployment at a bifurcation. In the stent in accordance with the invention there are therefore typically no parts of the stent that project into the lumen of the hollow organ. The formation of deposits or even the clogging of the hollow organ by deposits or blood clot formation are suppressed in this manner. Two sections of the bifurcation can be supported by the introduction of only one stent due to the two stent sections.

In general terms, the chamfered region allows a reliable support of the hollow member up to the bifurcation without, however, for example substantially projecting into the bloodstream after the bifurcation.

A cell can be connected to one or more other cells by a connection section of by a plurality of connection sections. As mentioned, a cell can comprise the total cut-out and its respective bordering elements, with the connection sections belonging to the bordering elements.

In a stent in accordance with the invention, at least some of the cells can be respectively connected to one another by means of a plurality of connection sections. Three or four respective connection sections can in particular be provided, whereby a radial placement force of the stent and thus its support effect can be particularly high.

The stent can be produced from a memory metal that adopts a stored shape from a limit temperature onward. The stent can be produced from nitinol for this purpose, for example.

The stent sections of the stent in accordance with the invention can be formed by two originally separate stents that are connected, in particular welded, to one another in the coupling section.

The first and second stent sections each have two ends, with the mutually facing ends being called the central ends and the mutually remote ends being called the lateral ends.

The connection by means of the coupling section can be configured such that the stent sections are movable with respect to one another and are in particular pivotable about the coupling section with respect to one another. It can be possible due to the pivotability to arrange the first longitudinal axis of the first stent section in parallel with the second longitudinal axis of the second stent section. The central ends can face one another in such an arrangement having parallel longitudinal axes.

On the deployment of the stent in accordance with the invention in a hollow organ, for example at the opening of the two venae iliaca communis into the vena cava inferior, in particular in the upper region of the venae iliaca communis, the alignment of the longitudinal axes of the stent sections can be modified to adapt the longitudinal axes to the direction of extent of the vein respectively accommodating the stent section. Stent sections can be pivoted about the coupling section for this purpose. For example, the first longitudinal axis and the second longitudinal axis can have an angle of approximately 0° to 70° toward one another in the deployed state. The chamfer of the first central end of the first stent section can comprise an angle of, for example, 10°, 15°, 25°, 35°, 45°, or 60° so that the first stent section—depending on the application—does not project into the bifurcation, but rather supports the hollow organ (i.e. e.g. the vena iliaca communis) up to the bifurcation. Said angles can here be present between the normals of the end planes (described below) of the first stent section.

In the example selected above, the first stent section can, for example, be disposed in the vena iliaca communis, whereas the second stent section is arranged in the vena cava inferior.

Preferred embodiments of the invention can be seen from the description, from the dependent claims and from the drawings.

In accordance with a first advantageous embodiment, the central and lateral ends define central and lateral end planes, with the lateral end planes being in parallel with one another when the first longitudinal axis and the second longitudinal axis are in parallel with one another.

In addition, the second central end plane can also be in parallel with the second lateral end plane.

It is alternatively also possible that the second central end and/or the first lateral end and/or the second lateral end is/are also formed as chamfered in addition to the first central end. Additional areas of use for the stent can hereby be opened up, for example in regions between two bifurcations.

The ends of the stent sections can each define end planes, that is can represent a virtual area that is fined by the respective last bordering elements of the stent sections in the direction of the longitudinal axis. The central end planes can have an angle toward one another due to the chamfer. In other words, a normal vector of the end plane of the first central end can include an angle with the longitudinal axis. This angle can, for example, be in the range between 10° and 60°, preferably between 30° and 40°.

In this respect, the end plane of the first central end is called the first central end plane, the end plane of the second central end is called the second central end plane, the end plane of the first lateral end is called the first lateral end plane, and the end plane of the second lateral end is called the second lateral end plane.

In accordance with a further advantageous embodiment, the first central end plane of the first central end of the coupling section includes the coupling section and has a decreasing distance from the first lateral end plane of the first lateral end as the distance from the coupling section increases. In other words, the chamfer of the first central end can be arranged such that the first stent section has the greatest longitudinal extent in the direction of the first longitudinal axis where the first stent section merges into the coupling section. The first central plane can therefore be inclined toward the first lateral end plane, whereas the first central end plane inclines away from the second lateral end plane when the longitudinal axes are in parallel with one another.

In accordance with a further advantageous embodiment, the first stent section and the second stent section are each only connected to one another at a longitudinal side and are pivotable with respect to one another. The longitudinal side is to be understood as the region of the respective stent section that has the longest extent in the direction of the respective longitudinal axis.

The coupling section can satisfy a hinge function to ensure the pivotability of the stent sections with respect to one another. The stent sections here can be pivotable about the coupling section.

In accordance with a further advantageous embodiment, the first stent section and the second stent section are each connected to the respective other stent section at a respective plurality of neighboring or mutually adjacent cells, preferably at exactly two such cells. The coupling section here can comprise the connected cells. A stable connection of the stent sections can be provided by the connection by means of two cells, with a pivotability of the stent sections with respect to one another nevertheless being maintained. In addition, a greater areal support of the tissue in the region of the coupling section can be carried out in this manner, whereby a collapse of the tissue can be avoided.

Alternatively, the first stent section and the second stent section can be connected to the respective other stent section at exactly one cell. An increased "movability" of the stent sections with respect to one another can be achieved by the connection at only one point since the stent sections can then be rotated against one another to a certain extent.

The stent can preferably be in one piece. This means that the stent sections are e.g. shaped from one piece of a common starting material. The stent sections can accordingly be formed from the same material.

In accordance with a further advantageous embodiment, at least one marker is provided at each end that in particular has the form of an eyelet into which a plate of radio-opaque material such as tantalum is inserted. The marker can serve to increase the visibility of the stent in the radiograph so that the position of the stent is easily recognizable in the radiograph. The marker can generally be a section of the stent that has an elevated impermeability to X-rays, whereby it is particularly easily visible in a radiograph.

Due to the application of a marker to each end of the stent sections, the two stent sections can easily be distinguished from one another in the radiograph and their alignments can be recognized.

The coupling section can preferably comprise at least one marker that in particular has the form of an eyelet. The coupling section can, for example, comprise exactly two markers that each an eyelet filled with or covered by e.g. tantalum, silver, niobium, tungsten and/or molybdenum. The coupling section can consequently be formed by one, two, or more markers, with the central ends being able to "share" the markers of the coupling section.

In accordance with a further advantageous embodiment, the cross-section diameter of the first stent section is smaller than the cross-section diameter of the second stent section in the expanded state. The second stent section is therefore suitable for supporting larger lumens, whereas the first stent section is suitable for lumens having a smaller diameter. The cross-section diameter of the stent sections can also be the same. In general, any desired combinations of cross-section diameters of the stent sections can be selected, with the cross-section diameter of the second stent section also being able to be smaller than the cross-section diameter of the first stent section.

The first and second stent sections can have cross-section diameters of greater than or equal to 12 mm. The first stent section can preferably have a cross-section diameter of 12 mm and the second stent section can preferably have a cross-section diameter of 18 mm.

The longitudinal axes can in particular be arranged offset from one another with a parallel alignment due to the different cross-section diameters. If, for example, the first stent section has a smaller cross-section diameter than the second stent section, the possibility arises of arranging an additional that neighbors the first stent section, that is adjacent to the second stent section, or that projects into the second stent section. The additional stent can serve to support both branches of a bifurcation. The additional stent can likewise have a chamfered end. For a simpler handling of the additional stent, it can be independent of the two stent sections and can be non-permanently fastened to the stent sections.

In accordance with a further advantageous embodiment, some of the cells of the first stent section are configured as elongated in the direction of the first longitudinal axis in comparison with the remaining cells of the first stent section to form the chamfered first central end.

A chamfered end can be produced due to the elongated cells. In this respect, due to the cells elongated in the direction of the first longitudinal axis, no additional cells are required to form the chamfered end. It is made possible by means of the elongated cells also to select a similar arrangement of the cells in the chamfered region as in the remaining tubular body of the first stent section.

The elongated cells can in particular only be present in a rigid section of the first stent section. In addition, the first stent section can, for example, comprise a flexible section and/or an anchorage section. The following statements with respect to the elongated cells relate to the rigid section.

A structure of the first stent section can result due to the avoidance of additional cells that can provide a particularly high radial placement force. It is made possible in this manner to reliably support blood vessels, for example, in proximity to bifurcations.

The dispensing with of additional cells further allows the angle of the chamfer to be fixed variably since this angle can be fixed by the relative elongation of the elongated cells on the manufacture of the stent.

The connection sections between the cells (that is between the elongated cells) can likewise be elongated with the elongated cells.

In accordance with a further advantageous embodiment, at least some of the elongated cells are arranged along a straight line or an approximately straight line that in particular extends in parallel or approximately in parallel with the first longitudinal axis.

Additionally or alternatively the elongated cells can be able to be divided into a plurality of groups, in particular into nine groups or into thirteen groups, with the cells of each group being respectively arranged along a straight or an approximately straight line, with the lines in particular extending in parallel or approximately in parallel with the first longitudinal axis.

Twelve or sixteen groups of cells can be provided overall of which nine or thirteen groups have elongated cells.

The arrangement of the cells can be selected such that the respective cells are arranged along straight lines or approximately straight lines. In addition, the cells can be formed symmetrically to one of these lines. There can in particular be no cells present that are inclined or rotated with respect to the other cells. A weakening of the structure by such rotated cells can be avoided in this manner. All the cells within a group can in particular each have the same length or approximately the same length viewed in the longitudinal axis. Alternatively, cells having different lengths can also be provided in a group.

The lines that are formed by the cells of different groups of the first stent section preferably extend in parallel or approximately in parallel with one another. The lines can additionally extend in parallel or approximately in parallel with the first longitudinal axis.

In accordance with a further advantageous embodiment, respectively the same number of cells is provided in each group from a cross-sectional plane extending perpendicular to the first longitudinal axis up to the chamfered first central end. A radial placement force can be effected by the provision of respectively the same number of cells in a group that is substantially constant over the length of the first stent section. The same number of cells can preferably be provided in each group in the rigid section of the first stent section.

Alternatively or additionally, the length of the cell of adjacent groups in the peripheral direction can fall from a maximum to a minimum. Cells having a maximum length are in particular disposed opposite cells having a minimal length with respect the first longitudinal axis of the stent. The chamfer can be produced by such an arrangement.

In accordance with a further advantageous embodiment, the first stent section comprises a flexible section in the region of the first lateral end. The flexible section can have cells that have a larger area than cells of the remaining first stent section. The flexible section can be more easily bendable due to the larger cells, whereby the flexible section can be more simply adapted to the shape of extent of a hollow organ. The cells of the flexible sections can preferably have a tooth-like boundary.

In accordance with yet a further advantageous embodiment, the first stent section comprises an anchorage section that adjoins the flexible section. The cells of the anchorage section can correspond to the cells of the rigid section and can, for example, be in diamond shape. The anchorage section can have a smaller flexibility due to the diamond-shaped cells and can thus fix the stent at its position in the hollow organ. The anchorage section can form a straight end of the first stent section, that is the end plane of the first lateral end has the first longitudinal axis as the normal vector. The markers of the first lateral end can accordingly be attached to the rigid section of the first stent section.

Figure 2:
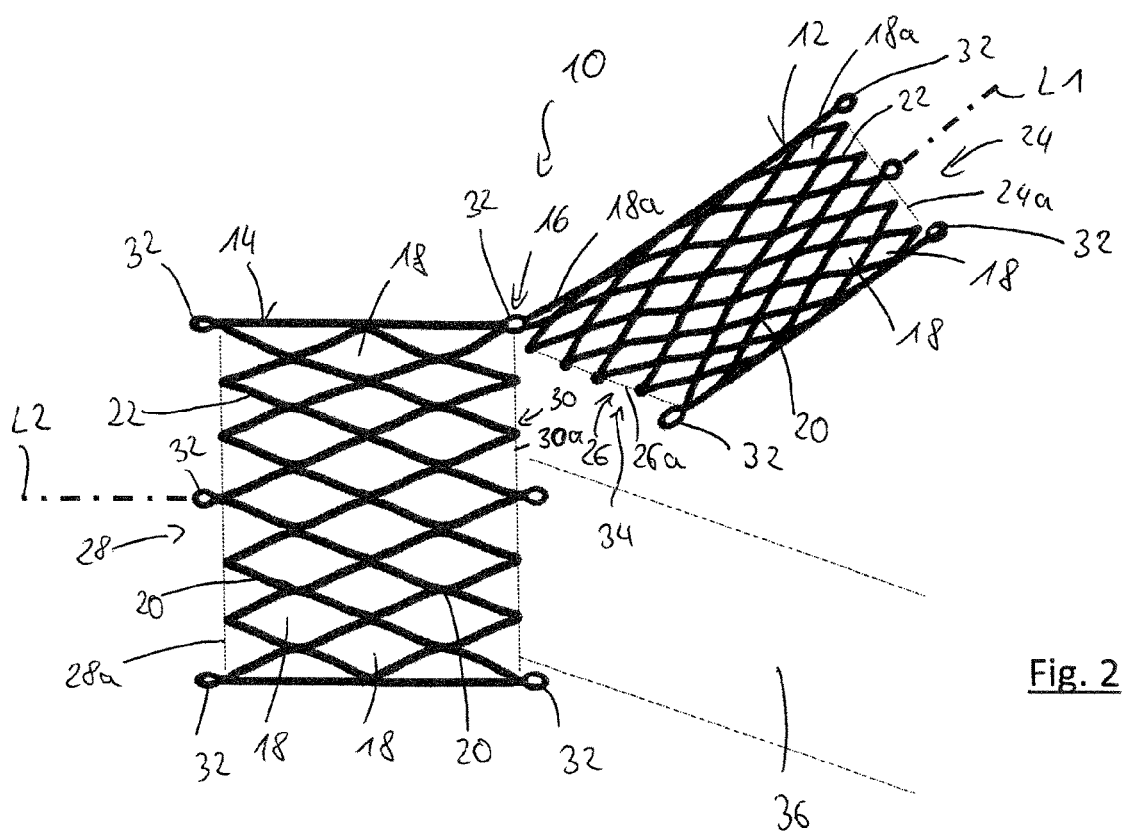

The invention will be described in the following purely by way of example with reference to the enclosed drawings. There are shown:

FIG. 1 a stent in accordance with the invention in the expanded state in a plan view; and FIG. 2 the stent of FIG. 1 in the expanded state in a side view with stent sections pivoted toward one another.

FIGS. 1 and 2 show a stent 10 that comprises a first stent section 12 and a second stent section 14. The first stent section 12 and the second stent section 14 are connected to one another by means of a coupling section 16.

The first stent section 12 and the second stent section 14 are each in the substantially tubular body that in particular has a circular cross-section, with the first stent section 12 extending along a first longitudinal axis L1 and the second stent section 14 extending along a second longitudinal axis L2.

In FIG. 1, the longitudinal axes L1, L2 extend in parallel with and coaxially to one another, whereas an arrangement of the stent is shown in FIG. 2 in which the longitudinal axes L1, L2 include an angle of approximately 35° with one another on projection onto the plane of the drawing. To achieve such an angle, the stent sections 12, 14 are pivoted about the coupling section 16. The arrangement of FIG. 2 approximately corresponds to the alignment of the stent sections 12, 14 on the deployment of the stent 10 at a bifurcation.

The stent sections 12, 14 are formed from diamond-shaped (closed) cells 18 that are each connected to other diamond-shaped cells 18 via three or four connection sections 20. The diamond-shaped cells 18 are defined by web-like bordering elements 22 that are shaped from a metal.

The first stent section 12 comprises a first lateral end 24 and a first central end 26. The second stent section 14 comprises a second lateral end 28 and a second central end 30.

The first lateral end 24 defines a first lateral end plane 24a. In a corresponding manner, the first central end 26 defines a first central end plane 26a, the second lateral plane 28 defines a second lateral end plane 28a, and the second central end 30 defines a second lateral end plane 30a. The end planes 24a, 26a, 28a, 30a are only shown in FIG. 2 for better clarity.

The central ends 26, 30 are adjacent to one another in the region of the coupling section 16, with a connection being established between the stent sections 12, 14, by two eyelets that serve as markers 32. Each of the markers 32 of the coupling section 16 here connects a cell 18 of the first stent section 12 to a cell 18 of the second stent section 14.

Further markers 32 are also provided at the first lateral end 24 and at the second lateral end 28. The markers 32 are filled with tantalum (not shown) to be easily visible in the radiograph. Silver, niobium, tungsten and/or molybdenum can also be used instead of or in addition to tantalum.

The cells 18 of the second stent section 14 are each formed uniformly so that the end planes 28*a*, 30*a*, that are defined by the second ends 28, 30 of the second stent section 134, extend in parallel with one another.

In the first stent section 12, in contrast, elongated cells 18*a* are provided that are elongated in the direction of the first longitudinal axis L1. A chamfer 34 is produced at the first central end 26 due to the elongated cells 18*a*. Two of the elongated cells 18*a* are connected to the markers 32 of the coupling section 16.

It can be made possible by the chamfer 34 that the first stent section 12 does not project into the lumen of the hollow organ to be supported on the deployment of the stent 10 at a bifurcation.

The chamfer 34 and the coaxial arrangement of the longitudinal axes L1, L2 further provide the possibility of inserting an additional stent 36 into the second stent section 14, as is indicated in FIG. 2.

REFERENCE NUMERAL LIST

- 10 stent
- 12 first stent section
- 14 second stent section
- 16 coupling section
- 18 cell
- 18*a* elongated cell
- 20 connection section
- 22 bordering element
- 24 first lateral end
- 24*a* first lateral end plane
- 26 first central end
- 26*a* first central end plane
- 28 second lateral end
- 28*a* second lateral end plane
- 30 second central end
- 30*a* second central end plane
- 32 marker
- 34 chamfer
- 36 additional stent
- L1 first longitudinal axis
- L2 second longitudinal axis

The invention claimed is:

1. A stent for transluminal implantation into hollow organs, the stent comprising:
    a first stent section having a substantially tubular first body that extends along a first longitudinal axis and that has a first lateral end and a first central end; and
    a second stent section having a substantially tubular second body that extends along a second longitudinal axis and that has a second lateral end and a second central end,
    wherein the first stent section and the second stent section are connected to one another with a coupling section in the region of the central ends;
    wherein the stent comprises a plurality of cells that are defined by bordering elements formed by the tubular bodies, with the tubular bodies each being able to be transformed from a compressed state having a first cross-section diameter into an expanded state having an increased second cross-section diameter,
    wherein the first central end of the first stent section is chamfered, and
    wherein some of the cells of the first stent section are more elongated in the direction of the first longitudinal axis in comparison with the other cells of the first stent section to form the chamfered first central end.

2. The stent in accordance with claim 1,
    wherein the central and lateral ends define central and lateral end planes, with the lateral end planes being in parallel with one another when the first longitudinal axis and the second longitudinal axis are in parallel with one another.

3. The stent in accordance with claim 2,
    wherein the first central end plane of the first central end includes the coupling section and has a decreasing distance from the first lateral end plane of the first lateral end with an increasing distance from the coupling section.

4. The stent in accordance with claim 1,
    wherein the first stent section and the second stent section are each connected to one another at a longitudinal side and are pivotable with respect to one another.

5. The stent in accordance with claim 1,
    wherein the first stent section and the second stent section are each connected to the respective other stent section at a respective plurality of cells neighboring or adjacent to one another.

6. The stent in accordance with claim 5,
    wherein the first stent section and the second stent section are each connected to the respective other stent section at exactly two cells.

7. The stent in accordance with claim 1,
    wherein the first stent section and the second stent section are each connected to the respective other stent section at exactly one respective cell.

8. The stent in accordance with claim 1,
    wherein the stent is formed in one piece.

9. The stent in accordance with claim 1,
    wherein at least one marker is provided at each end.

10. The stent in accordance with claim 9,
    wherein the at least one marker has the form of an eyelet.

11. The stent in accordance with claim 1,
    wherein the coupling section comprises at least one marker.

12. The stent in accordance with claim 11,
    wherein the at least one marker has the form of an eyelet.

13. The stent in accordance with claim 1,
    wherein the cross-section diameter of the first stent section is smaller than the cross-section diameter of the second stent section in the expanded state.

14. The stent in accordance with claim 1,
    wherein at least some of the elongated cells are arranged along a straight line or an approximately straight line.

15. The stent in accordance with claim 14,
    wherein the straight line or the approximately straight line extends in parallel or approximately in parallel with the first longitudinal axis.

16. The stent in accordance with claim 14,
    wherein respectively the same number of cells is provided in each group from a cross-sectional plane extending perpendicular to the first longitudinal axis up to the chamfered first central end.

17. The stent in accordance with claim 14, wherein a length of the cells of adjacent groups drops from a maximum to a minimum in the peripheral direction.

18. The stent in accordance with claim 1, wherein the elongated cells are divisible into a plurality of groups, with the cells of each group respectively being arranged along a straight line or an approximately straight line.

19. The stent in accordance with claim 18, wherein respectively the same number of cells is provided in each group from a cross-sectional plane extending perpendicular to the first longitudinal axis up to the chamfered first central end.

20. The stent in accordance with claim 18, wherein a length of the cells of adjacent groups drops from a maximum to a minimum in the peripheral direction.

21. The stent in accordance with claim 1, wherein the first stent section comprises a flexible section in the region of the first lateral end.

\* \* \* \* \*